(12) United States Patent
Pinteur et al.

(10) Patent No.: US 11,096,995 B2
(45) Date of Patent: Aug. 24, 2021

(54) THERAPEUTIC CANCER VACCINE BASED ON STRESS PROTEINS RENDERED IMMUNOGENIC

(71) Applicant: BRENUS PHARMA, Issoire (FR)

(72) Inventors: Benoît René Eugène Pinteur, Francheville (FR); Gilles Guy Devillers, Toulon (FR)

(73) Assignee: BRENUS PHARMA, Issoire (FR)

( * ) Notice: Subject to any disclaimer, the term of this patent is extended or adjusted under 35 U.S.C. 154(b) by 63 days.

(21) Appl. No.: 16/105,477

(22) Filed: Aug. 20, 2018

(65) Prior Publication Data

US 2019/0038731 A1 Feb. 7, 2019

Related U.S. Application Data

(63) Continuation of application No. 15/029,997, filed as application No. PCT/EP2014/072149 on Oct. 15, 2014, now abandoned.

(30) Foreign Application Priority Data

Oct. 15, 2013 (FR) ...................................... 1360031

(51) Int. Cl.
| | | |
|---|---|---|
| *A61K 35/13* | (2015.01) | |
| *A61K 39/00* | (2006.01) | |
| *C07K 14/47* | (2006.01) | |
| *C12N 5/09* | (2010.01) | |

(52) U.S. Cl.
CPC .......... *A61K 39/0011* (2013.01); *A61K 35/13* (2013.01); *A61K 39/001176* (2018.08); *C07K 14/4748* (2013.01); *C12N 5/0693* (2013.01); *A61K 2039/5152* (2013.01)

(58) Field of Classification Search
CPC ........ A61K 39/0011; A61K 39/001176; A61K 35/13; C12N 5/0693; C07K 14/4748
USPC ..................................................... 424/277.1
See application file for complete search history.

(56) References Cited

U.S. PATENT DOCUMENTS

| | | |
|---|---|---|
| 5,290,551 A | 3/1994 | Berd |
| 5,422,109 A | 6/1995 | Brancq et al. |
| 6,235,282 B1 | 5/2001 | Riviere et al. |
| 6,333,028 B1 | 12/2001 | Berd |
| 7,582,551 B2 | 9/2009 | Kodani et al. |
| 8,029,808 B2 | 10/2011 | Srivastava |
| 8,591,890 B2 | 11/2013 | Srivastava et al. |
| 9,248,172 B2 | 2/2016 | Srivastava et al. |
| 9,352,019 B2 | 5/2016 | Srivastava |
| 2002/0004052 A1 | 1/2002 | Berd et al. |
| 2005/0175635 A1 | 8/2005 | Colaco |
| 2006/0079458 A1 | 4/2006 | Srivastava et al. |
| 2008/0112962 A1 | 5/2008 | Palucka et al. |
| 2008/0286314 A1 | 11/2008 | Palucka et al. |
| 2009/0208524 A1 | 8/2009 | Srivastava et al. |
| 2012/0021996 A1 | 1/2012 | Srivastava et al. |
| 2012/0021997 A1 | 1/2012 | Srivastava et al. |
| 2013/0122049 A1 | 5/2013 | Palucka et al. |
| 2014/0107391 A1 | 4/2014 | Srivastava et al. |
| 2015/0231200 A1 | 8/2015 | Srivastava |
| 2017/0000455 A1 | 1/2017 | Nakai |

FOREIGN PATENT DOCUMENTS

| | | | |
|---|---|---|---|
| WO | WO 2000138710 | * 7/2000 | ............. A61K 39/00 |
| WO | WO 03090686 | 11/2003 | |

OTHER PUBLICATIONS

Dressel et al. (Cancer Research 63, 8212-8220, Dec. 1, 2003).*
Schmitt, et al, "Intracellular and extracellular functions of heat shock proteins: repercussions in cancer therapy", Jan. 2007, pp. 15-27, vol. 81, Journal of Leukocyte Biology.
Neckers, Len, "Heat shock protein 90: the cancer chaperone", Apr. 2007, pp. 517-530, vol. 32, No. 3, J. Biosci.
Ciocca, et al, "Heat shock proteins in prostate cancer: From tumorigenesis to the clinic", Dec. 2010, pp. 737-747, vol. 26, No. 8, Int. J. Hyperthermia.
Singh, et al., "Recent Advances in Vaccine Adjuvants", Jun. 2002, pp. 715-716, vol. 19, No. 6, Pharmaceutical Research.
Peters, et al, "Preparation of Immunotherapeutic Autologous Tumor Cell Vaccines Solid Tumors", Apr. 1979, pp. 1353-1360, vol. 39, Cancer Research.
Soo, et al, "Heat Shock Proteins as Novel Therapeutic Targets in Cancer", 2008, pp. 311-316, vol. 22, in vivo.
Ito, et al, "Heat shock protein 70 gene therapy combined with hyperthermia using magnetic nanoparticles", 2003, pp. 918-925, vol. 10, Cancer Gene Therapy.
Borst, et al, "A Family of Drug Transporters: the Multidrug Resistance-Associated Proteins", Aug. 16, 2000, pp. 1295-2000, vol. 92, No. 16, Journal of the National Cancer Institute.
Wirth, et al, "Les proéines de choc thermique (heat shock proteins-Hsps). II. Hsp70: biomarqueur et acteur du stress cellulaire.", 2003, pp. 127-144, vol. 147, Ann. Méd. Vét.
Gupta, Kusum R., "Immunology and Medical Microbiology", pp. 1-11.
Gilabert, et al, "Novel role of VMP1 as modifier of the pancreatic tumor cell response to chemotherapeutic drugs", Sep. 2013, pp. 1834-1843, vol. 228, No. 9, J Cell Physiol.

(Continued)

*Primary Examiner* — Yan Xiao
(74) *Attorney, Agent, or Firm* — B. Aaron Schulman, Esq.; Sttites & Harbison, PLLC

(57) ABSTRACT

The invention describes a method for preparing a composition comprising tumour cell stress proteins, said method comprising the following steps: providing tumour cells in a culture medium; subjecting the tumour cells under i) to a stress with the result that these cells produce stress proteins in response to the stress; obtaining or recovering stressed tumour cells and/or stress proteins; treating the stressed tumour cells and/or the stress proteins obtained with a molecule or a process capable of rendering the stress proteins immunogenic, preferably a hapten or haptenization. The invention also describes a pharmaceutical composition comprising tumour cell stress proteins and/or tumour cells comprising stress proteins, these stress proteins being rendered immunogenic, and are in particular haptenized, and a pharmaceutically acceptable excipient.

12 Claims, 4 Drawing Sheets

(56) References Cited

OTHER PUBLICATIONS

Figure 1:
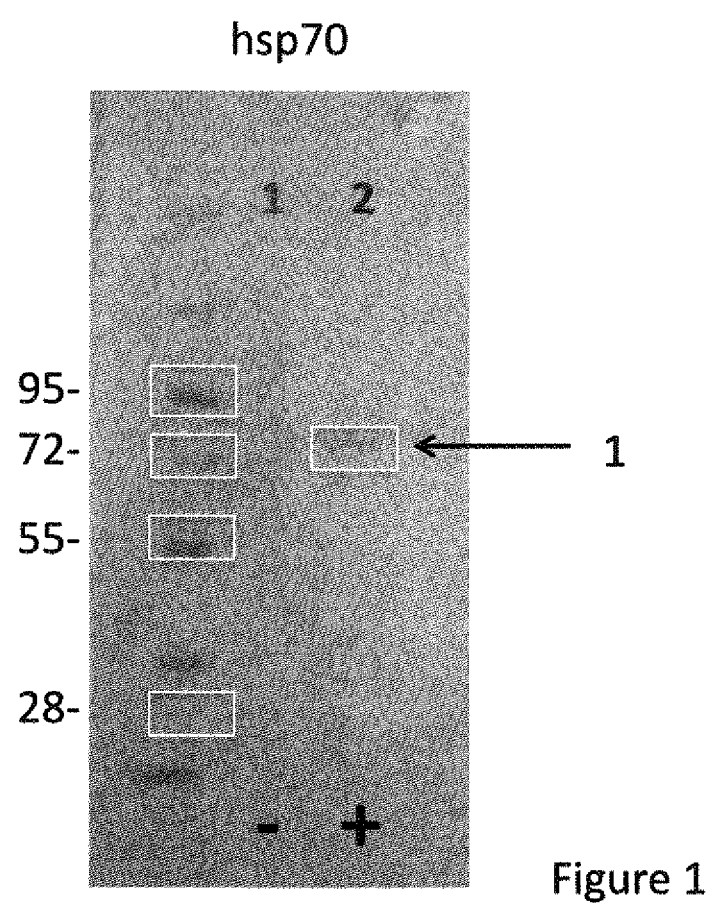

Garcia, et al, "Protéines HSP et cancer", Nov. 2011, pp. 1-46.
Clementi, et al, "Antibodies Against Small Molecules", 1991, pp. 139-144, vol. 27, No. 1, Ann Ist. Super Sanita.
Wirth, et al, "Les proéines de choc thermique (*heat shock proteins*). I. Classification, structure, fonctions et implications dans les processus pathologiques.", 2002, pp. 201-216, vol. 146, Ann. Méd. Vét.
Dutton, et al, "The Significance of the Protein Carrier in the Stimulation of DNA Synthesis by Hapten-Protein Conjugates in the Secondary Response", 1964, pp. 54-64, vol. 7, Immunology.
Ciocca, et al, "Heat shock proteins in cancer: diagnostic, prognostic, predictive, and treatment implications", 2005, pp. 86-103, vol. 10, No. 2, Cell Stress & Chaperones.
Centenera, et al, "Evidence for Efficacy of New Hsp90 Inhibitors Revealed by Ex Vivo Culture of Human Prostate Tumors", Jul. 1, 2012, pp. 3562-3572, vol. 18, No. 13, Clin Cancer Res.

\* cited by examiner

THERAPEUTIC CANCER VACCINE BASED ON STRESS PROTEINS RENDERED IMMUNOGENIC

CROSS REFERENCE TO RELATED APPLICATIONS

This application is a continuation of U.S. patent application Ser. No. 15/029,997, filed Apr. 15, 2016, which is a 371 application of International Application PCT/EP2014/072149, filed Oct. 15, 2014, and which claims the benefit of French patent application FR 1360031 filed Oct. 15, 2013, all of said applications incorporated herein by reference.

FIELD OF THE INVENTION

The present invention relates to a novel therapeutic approach to the treatment of cancer based on the stress proteins, "chaperone proteins", including such types as HSP and/or GRP or other proteins that are involved in the resistance mechanisms (LRPs, CTL4, PD-L1, etc.). It concerns in particular a method for preparing pharmaceutical compositions or therapeutic vaccines, the said pharmaceutical compositions or therapeutic vaccines themselves, and a treatment method for therapeutic treatment of cancer.

BACKGROUND OF THE INVENTION

The immune system is based on two defense mechanisms, namely, innate immunity, which is rapid but nonspecific; and acquired immunity, which is slower, but specific and has a memory. These two complementary mechanisms provide the ability to fight against internal "aggressions" by mobilizing the cells, either directly, during the cell-mediated immune response, or through the secretion of active molecules (of such types as immunoglobulins, cytokines, etc) during the humoral immune response.

Immunity is heavily involved in the occurrence and development of cancers. According to the three phases theory (3Es), the process of carcinogenesis is based on a dual immune function, the protective immunosurveillance process that is aimed at destroying the tumour cells and the "selection" of resistant cancer cells, in response to the mechanism of elimination. The three phases theory includes the first phase, referred to as elimination phase, during which the immune system fights against tumour proliferation entailing the involvement of tissue and environmental changes that are associated with the tumour (mobilisation of non-specific cells (macrophage, NK, s DC)), secretion of anti-proliferative, apoptotic, angiostatic molecules, production of cytokines, mobilization and activation of CD4 and CD8. During the second phase, referred to as the equilibrium phase in response to the immune system, the "sensitive" tumour cells are eliminated and the immune selection of the most resistant cells is brought about. The mechanisms of resistance that are set in motion are resistance to apoptosis, the secretion of inhibiting cytokines (TGF-β, IL-10, PGE2, IDO), alteration of the antigen presentation (partial or complete loss of expression of major histocompatibility complex (MHC) class I), the secretion of neutralising molecules, and MICA and MICB expression, a "counter-attack" of the cell mediated immune system by expression of Fas-L, PD-L1 leading to the death of T lymphocytes. During this phase, the number of tumour cell destroyed is in equilibrium with the number of resistant cells. This equilibrium phase corresponds to the remission phase observed during the treatments, it is also a selection phase for selecting the most virulent clones by their capacity to resist the immune defense system or the treatment. During the third phase, referred to as escape phase, the cells that are resistant to the various protective mechanisms of the immune system having developed one or more means of escape proliferate in the absence of any control. The cancer cells then develop a tumour mass that is the clinical manifestation of the physiological escape phenomenon. A related escape phenomenon is also observed in the advanced and metastatic stages of the cancers during the phenomena of resistance to the treatments.

The anti-cancer treatments include surgery, wherein the objective is primarily to remove or reduce the tumour, but this "mechanical" action does not have any real inhibitory effect on the process of carcinogenesis and is generally supplemented by various different treatment therapies aimed at "eliminating" the origin of the cancer. Radiation therapy is intended to bring about an alteration in the DNA of rapidly proliferating cells, which is the case with the tumour cells. The side effects of radiotherapy are twofold: even the healthy cells are irradiated, thereby causing the destruction thereof or genetic alterations which can lead to the "cancerization" thereof, and the tumour cells develop resistance to radiation-induced apoptosis by means of production of Chaperone proteins or chaperones (HSP, GRP, etc.) resulting in an escape phenomenon. Chemotherapy is intended to eliminate the tumour cells by acting either on the cells themselves, or by inhibiting specific metabolic pathways: direct interaction with DNA (electrophilic agents, intercalating agents, splitting agents), indirect interaction with DNA (inhibitors of DNA synthesis such as antimetabolites, topoisomerase inhibitors; inhibitors of spindle formation), neovascularisation inhibitors, proteasome inhibitors. Here again, resistance mechanisms are developed by the tumour cells and despite the poly-chemotherapy strategies implemented, relapse phenomena are observed with massive tumour proliferation, evidence of adaptability and a selection of cells that may be considered similar to the natural escape phenomena as described in the 3Es theory involving the immune system.

Immunotherapy comprises passive immunotherapy which consists of providing a significant amount of effectors, and active immunotherapy whereof the objective is to induce a specific immune response. Passive immunotherapy is based on the injection of antibodies so as to block a receptor, induce cell lysis, stimulate cytotoxicity, lift the inhibition of apoptosis (cetuximab-Erbitux®, Bevacizumab-Avastin®, Rituximab-Mabthera®, etc). The use of cytokines is another strategy to stimulate protective immune responses against the tumour (IL2, Infγ, etc). The objective of active immunotherapy or immunisation by vaccination is to immunize patients against cancer in accordance with different strategies: activation of the immune system by activation of dendritic cells, TLR agonists, tumour cell lysate, non-proliferating tumour cells either modified or not. These approaches constitute the new advanced-therapy medicinal products (ATMPs). They are promising and give good results, even more so if they are coupled with other treatments. The first active immunotherapy treatment to have been approved by the Food and Drug Administration (FDA) is Sipuleucel-T Provenge® based on the activation of the T lymphocytes (TLs) of the patient by culture in the presence of specific tumour antigens. However, with these treatments as well, escape phenomena are observed that are similar to the natural escape phenomena as described in the 3Es theory involving the immune system.

There thus continues to be a need to provide novel therapeutic strategies for the treatment of cancer, which can provide a specific inherent effectiveness and/or contribute to a multi-therapeutic strategy.

The various different anti-tumour mechanisms, although multiple, are all supported by the underlying strategy of the direct or indirect attack of tumor cells, with the ultimate step being the lysis of the cell or apoptosis thereof. The apoptosis resistance factor thus seems to be a key phenomenon because it induces a direct escape (inhibition of induced apoptosis) or indirect escape by protecting the tumour cells against intermediate mechanisms of destruction.

A number of studies have provided the means to better understand the resistance phenomena and in particular the role of "chaperone proteins" or stress proteins, in the resistance to apoptosis. In particular a known effect is the protective effect of Heat Shock Proteins (HSP 110, HSP 90, HSP 70, HSP 60, HSP 20, and ubiquitin) and GRP (glucose regulated proteins) GRP 94, GRP 78 (BiP), and GRP 58 localized mainly in the endoplasmic reticulum (also classified under the family of stress proteins). Emphasis has also been laid on the resistance factors that are related more specifically to the various treatments (Multi Drug Resistance) including therein the Multidrug Resistance Proteins (MRP) such as GP 170, VMP1, and LRP.

The mechanism of resistance to stress, and in particular to heat shock appears to be universal and present in all living organisms (bacteria, plants, animals). The function of the HSPs is characterized by the protective and reparative activity of certain proteins and enzymes by forming molecular complexes that inhibit the denaturation and the formation of "improper bonds" following as a result of "metabolic attacks" (hypoxia, low carbohydrate concentration, etc), aggressive physical attacks (thermal, radiation), or chemical/medication attacks.

At the present time there exist new strategies that use the HSPs as a therapeutic target. Some molecules have in particular been developed in order to try to inhibit HSP 90, but with mixed results and a high toxicity level. One of the more advanced therapies is the use of the small molecule 17-AAG (Tanespimycin or 17-allylamino-17-demethoxygeldanamycin; Len Neckers, Heat shock protein 90: the cancer chaperone J Biosci 32(3) April. 2007, 517-530, Indian Academy of Sciences), which inhibits the chaperone function of HSP 90 and whose clinical activity is promising, but with a number of side effects. Similarly, the small molecule Ganetespid (STA-9090), an inhibitor of the ATP site of HSP 90, is currently being tested in melanoma, as are other molecules that act on functions or on the HSP 90 sites (Novobiocin, Shepherdine, inhibitors of isoforms, etc.). Another target considered by the study is the lifting of the inhibition of apoptosis by acting on the HSP 70. The products under consideration are ADD70 (amino acid molecules), PES (2-phenylethylenesulfonamide), VER-155 008 (adenosine derivative) MKT077 (small molecule). Finally, the use of "OGX-427 antisense" directed against HSP 27 and Clusterin has been the subject of several clinical studies.

Furthermore reference has been made to the autologous use of HSP 70 or derivatives, as factor of immunization against tumour cells in mice. A Ménoret and J Hangman (Protéines de choc thermique et antigènes tumoraux/Heat Shock Proteins and Tumour Antigens, Medicine/Sciences 1994; 10: 665-71) describe the immunisation of mice against preparations of purified HSP 70 which are revealed to be immunogenic on condition of being associated with tumour peptides. Wirth D et al (Ann. Med Vet. 2002, 146, 201-216) mention studies that have shown that the vaccination of mice with a preparation of HSP or the transfer of tumour derived HSP 70 genes, immunizes them against an administration of autologous tumour cells and induces a regression of already developed tumours.

However, at the present time it appears that these approaches have a specific target focusing on either one or the other of the stress proteins without providing for a combined strategy that focuses on inhibition of the "entire set" of protection mechanisms developed by the tumour cells. Thus it has already been mentioned that the inhibition of HSP 90 would also result in a signal of defense by stimulating the secretion of other HSPs (Heat Shock Response) such as HSP 27 and HSP 70 thus enhancing the resistance to apoptosis and by inducing chemical-protections (A Ménoret and J Hangman 1994 as above).

SUMMARY OF THE INVENTION

The objective of the present invention is to provide a comprehensive overall approach, that is to say, which provides the ability to act simultaneously on multiple resistance mechanisms, preferably the entire set of these mechanisms which are developed by the tumour cells.

The objective of the invention is also to provide for the possibility of this approach being adapted to the stress or stresses to which the tumour cells are subjected in vivo, in particular in the course of the treatment protocol applied to a patient.

The objective of the invention is also to propose an approach that provides for a standardization related to the use of cell lines.

The objective of the invention therefore also relates to ensuring that this approach takes into account the type and/or the grade of the tumour cells, in particular those of the patient being treated.

The objective of the invention is thus also to propose such an approach that may in and of itself constitute a therapeutic protocol, or which is an adjuvant protocol of another therapeutic protocol.

The further objective of the invention is also to propose such an approach that is patient-specific.

The objective of the present invention is to stimulate the immune system by means of stress proteins that have been rendered immunogenic, in particular through haptenisation, in order to bring about the elimination of cells expressing the said resistance factors (stress proteins). This immunological treatment is aimed at eliminating or controlling the cells that can express these factors of resistance. The therapeutic approach proposed is intended in particular to be used against cancer on the basis of the following points:

the tumour cells develop mechanisms for resistance or escape when they are "stressed" naturally (immune system) or by means of a therapeutic protocol (radiation, chemotherapy, immunotherapy, etc.);

the resistance mechanisms entail the involvement of types of stress proteins like HSP, GRP and other proteins/glycoproteins;

the stress proteins are not by themselves naturally immunogenic in vivo, although they may under certain conditions engender "immunoprotection" by way of vaccination;

the specific anti-HSP (or anti-resistance factor) approaches seem also to be subjected to an escape phenomenon;

the protein environment (co-factor, substrate, etc.) appears to be an element to be taken into consideration in order to engender an anti-tumour protective effect by way of vaccination.

The invention thus concerns in particular a method for producing a composition that contains stress proteins induced by the application of a stress in vitro on a culture of tumour cells. More particularly, the said method produces such stress proteins in immunogenic form, that is to say capable of being recognized by the immune system of the patient and of leading the latter to develop an immune response against these proteins and the tumour cells that present such proteins. The method advantageously includes a step of inactivation of the tumour cells in order to render them non-proliferative. The invention also relates to compositions, in particular pharmaceutical compositions or therapeutic vaccines that contain such proteins. The invention also relates to methods of treatment against cancer by means of administration of such compositions, by way of principle therapeutic strategy or combined (in particular adjuvant) with another treatment protocol.

The invention relates to, and the method provides the ability to prepare, a pharmaceutical composition which comprises a plurality or all or the majority of the stress proteins expressed by the tumour cells under the conditions of the stress applied to them. This constitutes an advantage of the resulting product obtained which, by being representative of a plurality of stress proteins, allows the pharmaceutical composition to include a whole range of stress proteins rendered immunogenic that constitute further immunogenic elements against which the immune system of the patient will be able to react, and then target a whole panel of tumour cells and counteract the mechanisms of resistance that have variously been developed by these tumour cells under the pressure from the immune system and/or from the treatments applied.

Generally, these stress proteins will be found in the compositions according to the invention in one or more of the following forms: in the free state, in the state associated with the membrane of a tumour cell (including intra-membrane), presented at the surface of a tumour cell, present within the interior of a tumour cell, associated with a fragment of tumour cell or with a tumour peptide.

The composition according to the invention therefore will preferably include one or more of the identified stress proteins documented to date and at a given point in time. The following section presents several families thereof that are known to the person skilled in the art.

The HSPs are classified into six families according to their molecular weight, but their conformations and their characteristics within the same family seem to be variable according to their origin. Thus, of the HSP 70s (which include HSP 72 and 73 among others) the distinction can be made between those that respond to heat shock (HSP 70) and those that are very weakly affected by the heat stress (HSP 70).

The HSP 25/HSP 27, weakly expressed in normal cells, are overexpressed in tumour cells, and would play a role in the resistance to certain treatments and promote the growth and development of the proliferative tumour cells. Another role would be the inhibition of apoptosis by interaction with the pathway involving Caspase-3, regulation in the production of TNF-α, etc.

The family of HSP 47s is the one most recently identified, and has a role that is yet poorly defined. It would mainly participate in the development of connective tissues, in particular during the production of collagen. Being included among the "Heat Shock Proteins" its involvement in the resistance of tumour cells is likely, in particular, its participation during the neovascularization of tumours. HSP 40 would also play a role of "co-chaperone" in association with HSP70.

The HSP 60 (chaperonin) have been identified in bacteria (GroEL for Growth E. Coli large protein), and found in plants. These chaperone proteins participate in the tertiary conformation of the protein structure. This family of HSPs would play a role in immunity and in particular in autoimmune diseases.

The family of HSP 70s is one of the most studied families and it is along with HSP 90, the ones that are the most widespread. There exist several subclasses that would be either expressed by the cells in the 'normal' state, or induced directly following a stress. The characteristic features of these HSPs include their ability to interact with other proteins during their translation (folding), their participation in membrane transport, the inhibition of apoptosis as chaperone protein. The chaperone activity of HSP 70 is complex and entails the involvement of several factors such as HSP 40, Hip (Hsc Interactive Protein), Hop (Hsc-HSP 90 Organizing Protein) that enable the ATPase activity necessary for the formation of "chaperon-substrate" complexes. The anti-apoptosis action of HSP-70s is, it seems multifaceted and involves numerous inhibition/activation mechanisms on the pro-Caspase 9,8,3 pathways (inhibition), interaction with the p53 pathway (stabilization of the anti-P53 protein), inhibition of pro-apoptotic factors (Bax), regularization of cytochrome C, etc.

The HSP 90s are the most expressed constitutively and are present in all eukaryotes. They also come to be overexpressed during the phenomenon of stress and are targeted at the stabilization and the renaturation of proteins. Several isoforms have been identified according to their locations, their origins and their functionalities. The HSP 90s after dimerization have the ability to interact with the co-chaperones and thus form protein complexes that allow for the mutation and protection of molecules involved in tumoral transformation of cells (stabilization of specific proteins): P90 participates in the regulation of apoptosis (inhibition of Bcl-2, and Apaf-1), participates in cell proliferation and in metastasis (hTERT, MMP2), inhibits the p53, participates in the mutation by alteration then stabilization of the proteins.

The HSP 110s (or 105) are mainly induced as a result following stress. They would participate in the protection of ribosomes that are particularly sensitive during heat shocks. Their protective effect is mainly the dissociation of protein aggregates, their re-solubilization which allows for the reactivation of these proteins. The HSP 110s would seem to be a subgroup of the HSP 70s with identical binding domains and therefore certain similar properties.

The GRPs (Glucose Regulated Protein) constitute the other major group of stress proteins. Generally linked to the HSPs, their main role in the mechanisms of resistance is related to the protection of protein structures. Thus GRP 78 (BiP) would have a chaperone role with malformed proteins to be destroyed normally which thereby explains the resistance of cancer cells. GRP 75 known under the name "mortalin" would have an antiproliferative action in normal cells which, following its deregulation would participate in the cancerization of cells, while resulting in the opposite effect by inactivation of p53 participating in the regulation of apoptosis. GRP 94 also participates in the protection of incompletely assembled proteins whose three-dimensional conformation was imperfect. Related to HSP 70 it participates in the resistance to certain anti-cancer agents.

Other protein resistance factors, described as "Multi Drug Resistance", such as GP 170, MPRs (seven different ones), LRPs, and more recently VMP1 participate in the therapeutic escaping.

DETAILED DESCRIPTION

1. The Method of Preparation

An object of the invention therefore relates to a method for preparing a composition comprising stress proteins of tumour cells, which include the following steps:

v) providing (having) tumour cells in a culture medium;

vi) subjecting the tumour cells under i) to a stress and ensuring the result that these cells produce stress proteins in response to the stress;

vii) obtaining or recovering stressed tumour cells and/or stress proteins;

viii) treating the stressed tumour cells and/or the stress proteins obtained in iii) with a molecule or a process capable of rendering the stress proteins immunogenic, preferably a haptenisation process.

The culture medium may be a medium that makes it possible to maintain the viability of the cells and/or the growth or multiplication thereof. The media that are well-known to the person skilled in the art may be used. These media generally comprise a base culture medium "Minimum Essential Medium" that allow for cell survival wherein it is possible to add one or more mitogenic factors by means of serum or by using defined growth factors ("synthetic serum-free" medium). By way of example mention may be made of the following conventional media: DMEM, EMEM, HBSS, EBSS, PBS, RPMI, as well as others used for serum-free cell culture PANSERIN, EX-CELL® medium, etc., either supplemented or not with Glutamine, Insulin, HAM's nutrient, etc., to which may, if necessary, be added serum and/or growth factors.

The step ii) is preferably applied to a culture medium comprising tumour cells in growth phase or plateau phase. The person skilled in the art can readily determine that the cells are in one of these phases. In the first place, it is possible to determine in advance the culture conditions allowing to attaining these phases after a determined time period. It is also possible to determine that these phases have been attained by means of the following methods: cell growth curve, viability, doubling time, metabolite assay, or nutrient consumption, etc.

The stress is applied in vitro. It may be of any kind, in terms of chemical or physical nature, and the time period for application of the stress may vary in proportions that depend on the type of stress applied, the nature and application time period for each being chosen in order to ensure that the tumour cells produce stress proteins to a level that is appropriate for the invention, for example so as to take into account the anticancer protocol being applied to the patient. The following methods may be used:

radiation, in particular radiation between around 0.25 and around 25 gray, preferably low dose, that is to say between around 1 and around 5 gray, for example around 2 gray; the irradiation time period may be comprised between around 1 and around 20 min, preferably between around 1 and around 5 minutes;

heat shock, for example progressive graduated or sudden application of a temperature that is greater than 37° C. and sufficient to induce a stress which serves the purpose of producing thermal stress proteins; this temperature may be between around 38° C. and around 45° C., preferably between around 40° C. and around 43° C.; the holding time at this temperature may be between around 20 and around 100 minutes, preferably between around 30 and around 60 minutes; the rise in temperature may last from around 1 to around 5 minutes, for example around 3 minutes, chemical shock with a substance that is used for inducing a stress which serves the purpose of producing chemical stress proteins; among the substances that are usable mention may be made of alcohols such as ethanol (generally used at concentrations from around 10% to around 50% v/v); the anti-tumour substances used in chemotherapy, in particular of such types as alkylating agents, intercalating agents, for example cyclophosphamide, doxorubicin, breaking agents for DNA, for example, cisplatin; in one embodiment, use is made of one or more or all of the medicinal substance(s) used in the chemotherapy protocol that is standard for the type of cancer considered or in the protocol applied to the patient; the time period for bringing about contact may range from around 1 to around 48 hours, preferably from around 20 hours to around 26 hours; it is also possible to apply at least two of these chemical stresses;

metabolic stress, such as hypoxia, pH (in particular by acidification beyond pH 6.5), deficiency in a substance useful for the growth or survival of tumour cells, for example glucose, deficiency in a substance essential to the growth or survival of tumour cells, for example, electrolytes (balance of sodium, potassium, calcium, etc.); it is also possible to apply at least two of these metabolic stresses;

a combination of at least two of these types of stresses.

The conditions for each type of stress can be easily determined, with the aim of stressing these living cells in order to obtain the production of stress proteins, without inducing apoptosis or the death of the tumour cells or of too many of them, as has been indicated here above. The methods of Western blot and FACS cytometry for example make it possible to monitor the production of particular stress proteins, for example HSP, by using antibodies directed against these proteins. Such antibodies are available, as will be discussed further below in respect of some examples of HSP. It is also possible to check by means of routine tests in vitro (for example dose-effect tests) whether the conditions of a stress are too drastic, resulting in the death of the tumour cells.

According to a characteristic feature, when more than 1 stress is applied, it is preferable to apply them in succession. Preferably, the first stress is applied, then a lag phase is subsequently observed before applying the subsequent stress, and so on depending on the number of stresses. Advantageously, a centrifugation is carried out after the first stress, then a wash, a centrifugation, then followed by addition of fresh medium, lag phase, then the subsequent stress, etc.

According to one characteristic feature of the method of the invention, it is possible to confirm the expression or the production of factors of resistance or stress protein and even quantify the same. The person skilled in the art has at their disposable the means enabling it, such as analysis by flow cytometry, for example, FACS, ELISA, Western blot, etc. They can confirm the expression or production of the types of stress proteins, from their membership in a particular family, and even identify and quantify the particular type.

According to a characteristic feature of the method of the invention, the step iii) may be followed by a step iii-i) in which the resulting outcome of the previous step is treated in accordance with one or more of the following modalities: concentration of solid and proteinaceous materials, including stress proteins and tumour cells and fragments thereof, separation or purification of stress proteins or tumour cells, separation or purification of tumour cells and stress proteins, extraction of stress proteins.

According to the invention, the stress proteins may be divided into intracellular, extracellular free, intramembrane (cell or cell fragment), at the surface of a cell or a cell fragment. In general, the stressed cancer cells include intracellular stress proteins and surface stress proteins.

According to an important characteristic feature of the method, in step iv) a treatment process is carried out that makes it possible to render the stress proteins immunogenic or immunocompetent, that is to say capable of generating in vivo an immune response against them.

The time interval between the end of the step of applying the stress and the beginning of the subsequent step is sufficient for the tumour cells to have produced the stress proteins. This interval can be determined by varying the said time interval and determining or measuring the change in the expression of stress proteins. For example, the methods of Western blot and flow cytometry, e.g. FACS, using the specific antibodies for the proteins to be monitored (see below), may be employed. This interval is preferably several hours, and it may in particular be comprised between about 5 hours and about 24 hours. This interval may be less than 5 hours, it is possible to determine it by monitoring the production of stress proteins, by using the methods described herein, Western blot and FACS cytometry. It may also be longer than 24 hours, but such a long period may not be necessary, this can also readily be determined using the methods of the abovementioned measures.

According to the invention, a molecule that provides the means to confer immunogenicity to the stress proteins is introduced into the product resulting from iii) or iii-i). This step iv) in vitro provides the ability for example to chemically bond the said molecule to the proteins present, whether the latter are free or present on the surface or within the interior of a cell membrane or a cell structure, for example a tumour cell or a tumour cell fragment. Typically, the molecule, for example of haptenisation, is a molecule that is not naturally present in the tumour cells or in its environment ("non-naturally occurring molecule").

The person skilled in the art knows the procedures that make it possible to render the proteins (in particular haptenisation) immunogenic and may thus implement this step without difficulty. It is a means to make the haptens immunogenic, by combining an immunogenic molecule (a "carrier") and a hapten (in the case in hand the stress proteins) bonded in a covalent manner to this molecule.

Any carrier molecule or mixture of known carrier molecules may be used. By way of examples mention may be made of: Dinitrophenyl, 2,4-Dinitrofluorobenzene (DNFB), sulfanilic acid, N-iodoacetyl-N'-(5-sulfonic-naphthyl) ethylene diamine (EDA), aniline, p-amino benzoic acid, and mixtures thereof. The person skilled in the art may refer to the works of K Landsteiner (Specificity of Serological Reactions, 1945, Chap. V, Harvard University Press). The "carrier" molecules are capable of penetrating the membrane of the cell and reaching the cytosol. In the invention, the free stress proteins, the intracellular stress proteins and those bonded to the cell membranes are haptenised.

The haptenisation step includes the incubation in vitro of the stressed cells and the carrier molecule. Typically, the incubation may last from around 15 minutes to around 1 hour, in particular around 20 minutes to around 40 minutes.

This step is preferably carried out under mild agitation that provides the ability to maintain the cells in suspension or under a certain agitation condition.

According to one characteristic feature of the method of the invention, the step that is used to render the proteins immunogenic (for example haptenisation) step iv) may be followed by a step iv-i) in which the resulting outcome of the previous step is treated in accordance with one or more of the following modalities: concentration of solid and proteinaceous materials, including stress proteins and tumour cells and fragments thereof, separation or purification of stress proteins or tumour cells, separation or purification of tumour cells and stress proteins, extraction of stress proteins.

Depending on the nature of the stress and the intensity thereof, the tumour cells may be more or less degraded or fragmented. The main objective of the invention is not to degrade or fragment these cells, but to lead them to express their panoply of stress proteins. This signifies that a certain proportion of tumour cells may remain viable.

This is the reason why, according to another characteristic feature of the invention, a step that serves the purposes of inactivating the viable cells may be provided for. This step referred to as the inactivation step is carried out downstream of the application of the stress and after a time period that is sufficient for the cells to have expressed the stress proteins.

According to a first embodiment, the product derived from the step that is used to render the proteins immunogenic step iv) or step iv-i) may be treated, in particular inactivated, (step v)), in order for the tumour cells possibly present to be rendered non-proliferative.

According to a second embodiment, it is the product derived from the stress step which may be treated, in particular inactivated, (step v)) in order for the tumour cells possibly present to be rendered non-proliferative. In this case, the inactivation is placed between steps ii) and iv).

Any inactivation treatment known to the person skilled in the art may be employed, provided that it ensures the means that cause the tumour cells to lose their ability to proliferate in vivo when the composition is administered to the patient. This inactivation can be achieved in particular by means of a chemical treatment process (ethanol fixation) or by means of a physical treatment process, for example high dose radiation (for example about 25 gray). It is possible to determine the right conditions for inactivation, by carrying out cell culture tests, in order to determine the conditions that lead to a total lack of viability. It is also possible to use propidium iodide which provides the ability to distinguish between living cells and dead cells, as is known to the person skilled in the art. It is also possible for example, to use the test with propidium iodide followed by culturing as described here below.

According to another characteristic feature of the invention, the product derived from the step iv) or from the step v) is formulated by mixing of the product rendered immunogenic (haptenized protein material and/or haptenised cells and/or haptenized cell fragments) with a pharmaceutically acceptable vehicle or excipient and possibly an adjuvant. Preferably, the step includes the mixing with a pharmaceutically acceptable vehicle or excipient and an adjuvant.

The method provides the ability to prepare a pharmaceutical composition which comprises a plurality, or all, or the majority of the stress proteins expressed by the tumour cells under the conditions of the stress applied to them. This constitutes a first advantage to the resulting product obtained which, by being representative of a plurality of stress proteins, allows the pharmaceutical composition to include a whole range of stress proteins rendered immunogenic against which the immune system of the patient will be able to react, and then target a whole panel of tumour cells and counteract the mechanisms of resistance that have variously been developed by these tumour cells under the pressure from the immune system and/or from the treatments applied.

In order to enable a response to the various different stresses and to maintain the protein environment, the product to be subjected to the stress is preferably composed of whole tumour cells. The tumour cells used in step i) may be patient cells, derived from biopsies, possibly cultured or maintained live, possibly pools derived from various different patients, in particular allogeneic cells (same cell type); cells from the patient (autologous cells); allogeneic cells from pre-established lines or produced from patient cells, or mixtures of such cells; mixtures of these different types of cells.

In one particularly suitable embodiment, these whole cells are advantageously from cell lines, and in particular from lines of the same type as the tumour of the patient to be treated (allogeneic cells). These cells are "stimulated" by one of the stress factors, thereby enabling the overexpression of resistance factors. For example, a line may be subjected to a heat shock, a chemical agent, an irradiation, a metabolic stress or to a plurality of these stresses during the culturing thereof. The "stimulated" lines or the raw untreated or treated product derived from the stress protocol, are then rendered immunogenic in order to enable the recognition of the stress proteins by the immune system. In order to have an optimal representativeness of the resistance factors, several lines, in particular allogeneic, may be used.

In one embodiment, from the same population of tumour cells, groups of cells are subjected to various different stresses. It is possible for example to subject a first portion of the cells to one type of stress protocol selected from those described here above, and then subject a second portion of the cells to one of the other stress protocols (nature of stress may be different or same nature of stress but with different conditions), etc. They may then be used in the form of a kit-of-parts for administration, which may be simultaneous, separate or staggered over time. They may also be mixed. A pharmaceutical composition is made available which contains stress proteins that are potentially specific to each of the mechanisms of resistance depending on the type and/or the stress conditions applied (for example irradiation, thermal, chemical, metabolic, etc.).

In one embodiment, the method is applied to a mixture of allogeneic tumour cells, that is to say of the same tumour type, or by way of a variant, the method is applied separately to at least two populations of allogeneic tumour cells, then the products obtained that have been rendered immunogenic are mixed in order to constitute the pharmaceutical composition. The invention therefore makes it possible to provide such a solution which allows for a targeted approach based on the type of tumour cell, that is to say, the use of different cell types, but all deriving from the same type of cancer in order to potentiate the common immune reactions against the resistance factors expressed by all of these cells of one same given type of tumour (allogeneic cells), or expressed specifically by certain tumour cells.

In another embodiment, in order to maintain the specific protein environment of the patient's tumour, the cells derived from this tumour (autologous cells) are maintained in a medium thereby providing for their viability and/or growth, and then subjected to one (or more) of the stresses cited. The autologous cells thus stimulated express the stress proteins, which are then rendered immunocompetent, for example, during the subsequent haptenisation.

In this embodiment, the method is applied to a mixture of autologous tumour cells, that is, say, to the tumour cells originating from the patient to be treated, or by way of a variant, the method is applied separately to at least two populations of autologous tumour cells. They may then be used in the form of a kit-of-parts for administration, which may be simultaneous, separate or staggered over time. They may also be mixed. The invention therefore makes it possible to provide a personalized therapeutic approach, specific to the individual who has developed the tumour in order to maintain the factors of resistance and the protein environment specific to the patient's tumour by using autologous cells.

In another embodiment, the previous solutions are combined, with the kit-of-parts or mixtures of autologous cells and allogenic cells, the autologous and allogeneic cells preferably being allogeneic to each other, or with the mixture of products thereof rendered immunogenic according to the method of invention.

When working from the patient tumour cells, it is preferable to begin with the cells isolated from a biopsy or resection.

Preferably, the composition containing immunogenic stress proteins, and/or, preferably and, inactivated tumour cells is frozen or lyophilized.

2. The Compositions According to the Invention

The object of the present invention therefore also relates to a composition that may be obtained or produced by the method of the invention.

The compositions of the invention are characterized by the fact that they include stress proteins that are rendered immunogenic in accordance with the invention, in particular haptenised. This composition may also be characterized by the fact that it includes tumour cells which are those that have produced the stress proteins in response to the stress according to step ii), in particular tumour cells and/or debris or fragments of such cells that have been produced by the said method. This composition may comprise immunogenic stress proteins, in particular haptenised, that are free and/or immunogenic stress proteins, in particular haptenised, that are presented on the surface or within the interior of the tumour cells or fragments thereof. Preferably, the compositions of the invention include inactivated tumour cells and immunogenic stress proteins, which are in particular haptenised.

These compositions include a plurality, or all, or the majority of the stress proteins expressed by the tumour cells in vitro following as a result of a stress applied to them, and they are in an immunogenic form, in particular haptenised. In particular, when talking about "stress proteins", reference is being made to at least two different stress proteins, preferably 2, 3, 4, 5, 6, 7, 8, 9, or 10, or even more stress proteins, this varying based on the cell type and on the stress or stresses applied in vitro.

In various embodiments, the composition contains one or more heat shock proteins, in particular chosen from those described here above, for example HSP 27, HSP 70 or HSP 90; HSP 27, HSP 70 and HSP 90; HSP 27 and HSP 70; HSP 90 and HSP 27; HSP 90 and HSP 70. In these compositions, this or these HSPs is/are rendered immunogenic, in particular haptenised.

In other embodiments, the composition comprises one or more proteins with pleiotropic resistance to drugs, in particular proteins with resistance to chemotherapy (MRP, multidrug resistance-associated protein), for example GP 170, the MPRs (seven different proteins), the LRPs and/or VMP1.

In other embodiments, the composition comprises proteins with radiation resistance or even proteins with resistance to metabolic stress.

In other embodiments, the composition comprises GRPs, such as GRP 78 (BiP), GRP 75 and/or GRP 94.

In accordance with the teaching of the invention, the composition may include stress proteins of several of these categories.

The invention relates more particularly to a pharmaceutical composition or a therapeutic vaccine or an immunogenic composition comprising stress proteins that are rendered immunogenic, preferably haptenised.

These stress proteins may be in the free state, in the state associated with the membrane of a tumour cell (including intra-membrane), presented on the surface of a tumour cell, present within the interior of a tumour cell, and/or associated with a fragment of tumour cell or with a tumour peptide.

According to one characteristic feature, the composition comprises stress proteins that are rendered immunogenic, preferably haptenised.

According to another characteristic feature, the composition comprises tumour cells which are those that have produced stress proteins in response to the stress according to the step ii), including inactivated tumour cells. These cells may include and advantageously do include intracellular stress proteins, that are haptenised or otherwise rendered immunogenic in accordance with the invention. In vivo, these intracellular immunogenic stress proteins will in particular be presented to the immune system by the antigen presenting cells.

More particularly, the composition contains tumour cells and/or fragments of these cells, containing and/or bearing immunogenic stress proteins, that are preferably haptenised.

According to one characteristic feature, the composition contains both immunogenic stress proteins, that are free and preferably haptenised, and tumour cells and/or fragments of these cells, containing and/or bearing immunogenic stress proteins, that are preferably haptenised.

For use as a product that can be administered to a patient, these cells are rendered incapable of proliferation, this being referred to as inactivation.

This composition may also include a pharmaceutically acceptable vehicle or excipient.

In one embodiment, the composition comprises a population of immunogenic stress proteins, that are preferably haptenised and/or cells containing such proteins, which have been subjected to a first protocol of stress, and at least one other population of immunogenic stress proteins, that are preferably haptenised and/or cells containing such proteins, which have been subjected to another protocol of stress.

In one embodiment, the composition comprises a population of immunogenic stress proteins, that are preferably haptenised and/or cells containing such proteins, and at least one other population of immunogenic stress proteins, that are preferably haptenised and/or cells containing such proteins, the populations being derived from initial allogeneic tumour cells and these cells having been subjected to a protocol of stress as a mixture or separately.

In one embodiment, the composition comprises immunogenic stress proteins, that are preferably haptenised and/or cells containing such proteins, derived from initial autologous tumour cells.

In one embodiment, the composition comprises immunogenic stress proteins, that are preferably haptenised and/or cells containing such proteins, that are allogeneic and autologous.

In one embodiment, the composition comprises immunogenic stress proteins, that are preferably haptenised and/or cells containing such proteins, that are allogenic and autologous, for simultaneous, separate or staggered over time administration. The composition may be constituted of multiple doses of stress proteins that have been rendered immunogenic and/or cells containing allogeneic stress proteins that have been rendered immunogenic, in particular derived from different lines (1, 2, 3, . . . lines) and multiple doses of stress proteins that have been rendered immunogenic and/or cells containing autologous stress proteins that have been rendered immunogenic.

The compositions according to the invention are useful as anti-cancer drugs.

According to one characteristic feature, they are useful as anti-cancer drugs for administration to a patient who has undergone an anti-cancer treatment. As explained here above, this treatment would have resulted in a stress and therefore the production of stress proteins. The patient thus bears tumour cells presenting stress proteins.

According to another characteristic feature, the compositions are useful as anti-cancer drugs for administration to a patient who is undergoing or will undergo anti-cancer treatment. As explained here above, this treatment is likely to result in a stress and therefore the production of stress proteins. The patient whose treatment is ongoing either already has or is suspected to have tumour cells presenting the stress proteins.

According to one characteristic feature, the composition in addition comprises an adjuvant.

The adjuvant is a substance which acts by increasing the efficacy of a vaccine. This substance may act by accelerating, by prolonging and/or by augmenting the immune responses specific to an immunogen when this substance is used in combination with this specific immunogen. The person skilled in the art may refer in particular to Recent Advances in Vaccine Adjuvants, Singh M & O'Hagan D T, Pharmaceutical Research 2002, Volume 19, issue 6, pp 715-728. Among the possibly usable adjuvants, mention may be made of cytokines and other immunomodulation molecules (that is, chemokines and co-stimulatory factors), adjuvant substances derived from microorganisms and plants, or which are chemically synthesized. Depending on their nature, the adjuvants can act not only as immunostimulatory adjuvants but also as a vaccine delivery system. These delivery systems are generally particulates and mention may be made, in particular, of emulsions, microparticles (for example based on polylactide-glycolide PLG), ISCOMs, liposomes, which serve the purpose mainly of orienting and guiding the immunogens to the antigen presenting cells. As for the immunostimulatory adjuvants, they are mainly molecules of microbiological origin, for example lipopolysaccharide, monophosphoryl lipid A, CpG DNA, which activate the immune system. Adjuvants may also be used for delivery by means of the mucosal pathway, for example, bacterial enterotoxins, in particular deriving from *E. coli*, heat-labile enterotoxins, detoxified mutants such as K63 or R72.

By way of representative useable adjuvants mention may be made, among others, of: aluminum hydroxide, saponins (for example Quillaja saponin or Quil A; see Vaccine Design, The Subunit and Adjuvant Approach, 1995, edited by Michael F. Powell and Mark J Newman, Plennum Press, N Y and London, p 210), Avridine® (Vaccine Design p 148), DDA (Dimethyl Dioctadecyl Ammonium Bromide, Vaccine Design p 157), polyphosphazene (Vaccine Design p 204), oil-in-water emulsions, in particular those comprising a mineral oil, squalane (for example SPT emulsion, Vaccine Design p 147) or squalene (for example MF59, Vaccine Design p 183), water-in-oil emulsions, in particular those comprising a metabolisable oil (see particularly WO9420071), an emulsion according to U.S. Pat. No. 5,422,109, or a triple emulsion, for example a water-in-oil-in-water emulsion.

The term "pharmaceutically acceptable" is used to refer to a vehicle or excipient that can be used for administering an immunogen to a patient without risk of any allergic or other adverse reaction while also preserving the characteristic features of the product during storage thereof. This includes, for example, alone or in mixture, water, saline solutions, phosphate buffers, protein compounds, dextrose, sucrose, glycerol, DMSO, ethanol and the like. Mention may be made for example, of a saline solution with 0.9% NaCl, a phosphate buffer, a mixture based on commercially available preservative solutions.

In one embodiment, the composition according to the invention is intended to be frozen, in particular between −20° C. and −80° C. Then at least one cryoprotective agent is added to the composition, and/or the composition is prepared in the usual manner in order for it to tolerate the freezing without damage to its components, in particular the tumour cells.

In another embodiment, the composition according to the invention is intended to be lyophilized (freeze-dried). Then as may be necessary, at least one usual excipient for lyophilization is added.

The composition of the vehicle or excipient and/or the choice of the adjuvant may vary depending on the route of administration, as is known to the person skilled in the art.

3. Use and Method of Treatment

The product developed by the invention may have a variable composition, however insofar as it has characteristic features such as can be retained, it is that it includes stress proteins that have been induced in vitro by the subjecting of live tumour cells to one or more controlled stress(es), that these stress proteins are found at high concentration levels due to their overexpression by these tumour cells in response to the stress, and that generally these stress proteins are multiple in type, that these stress proteins in the final product that can be administered to the patient, are haptenised or otherwise treated so as to render them immunocompetent (immunogenic).

The principle underlying the invention is based on the capacity and ability of the immune system to develop a specific response against the resistance factors of the tumour cell (stress proteins) after having been stimulated by the presence of stress proteins that have been rendered immunocompetent (immunogens), for example being haptenised. This immune reaction eliminating the tumour cells, completes the actions initiated during the prior treatments (adjuvant action of the composition according to the invention) or enables the activation of the immune response as the principal treatment.

The object of the invention also relates to a method of therapeutic treatment. This method comprises administration of an effective amount of a composition according to the invention in order to provoke the immune response.

The dose administered may for example comprise from $10^5$ to $10^7$, in particular at least $10^6 \pm 0.5$ cells per dose. This quantity of cells can be expressed as total tumour cells, in tumour-originated carbon (TOC) or in terms of protein quantification.

The dosage regimen may include one or more dose administrations separated over time. For example, the regimen may provide for 2, 3, 4, 5, 6, 7, 8, 9 or 10 administrations spaced out over an interval of 1 to 10 days between each administration.

Any route of administration may be employed. Thus the routes that may be cited include oral, nasal, rectal, and parenteral routes. The parenteral route is preferred, in particular via intramuscular-, intravenous-, intraperitoneal-, subcutaneous-, and intradermal injection. Intradermal injection is particularly selected.

The treatment may be supplemented with the administration of immunostimulant(s) of any type, thus providing for the potentiation thereof (cytokine, growth factor, immunomodulator, adjuvant . . . ), whether or not the therapeutic composition has already been adjuvanted.

The method for treatment may include the combination of a treatment according to the invention with a conventional anti-cancer treatment protocol: surgery, radiation therapy, chemotherapy and/or immunotherapy. The compositions according to the invention are administered to the patient before, during or after one or more of these protocols. With regard to the induction of an immune response, it is however advantageous to administer the composition according to the invention before or during the conventional protocol, preferably before.

It is particularly feasible to envisage treating the patient with the allogeneic lines that have expressed the stress proteins in relation to the future conventional treatment, in order to stimulate the immune system in advance so as to obtain a response against the stress proteins potentially expressed in vivo and inhibit the resistance to the conventional treatment. For example, administration of the composition according to the invention, comprising radiation-induced stress proteins and/or cells that express radiation-induced stress proteins, prior to a radiation therapy treatment and/or administration of the composition according to the invention, comprising chemically induced stress proteins and/or cells that express the chemically induced stress proteins, by using preferably the anti-cancer therapeutic molecule as initiator of the stress, prior to a chemotherapy treatment with this molecule.

BRIEF DESCRIPTION OF THE DRAWING FIGURES

The present invention will now be described in greater detail with the aid of examples provided by way of non-limiting examples and with reference being made to the Figures.

FIG. 1 is a Western Blot showing the induction of the expression of HSP 70 by a thermal stress. In order to ensure ease of reading, the main calibration spots and HSP 70 spots have been encircled, with the latter being identified by the reference numeral 1.

Figure 2:
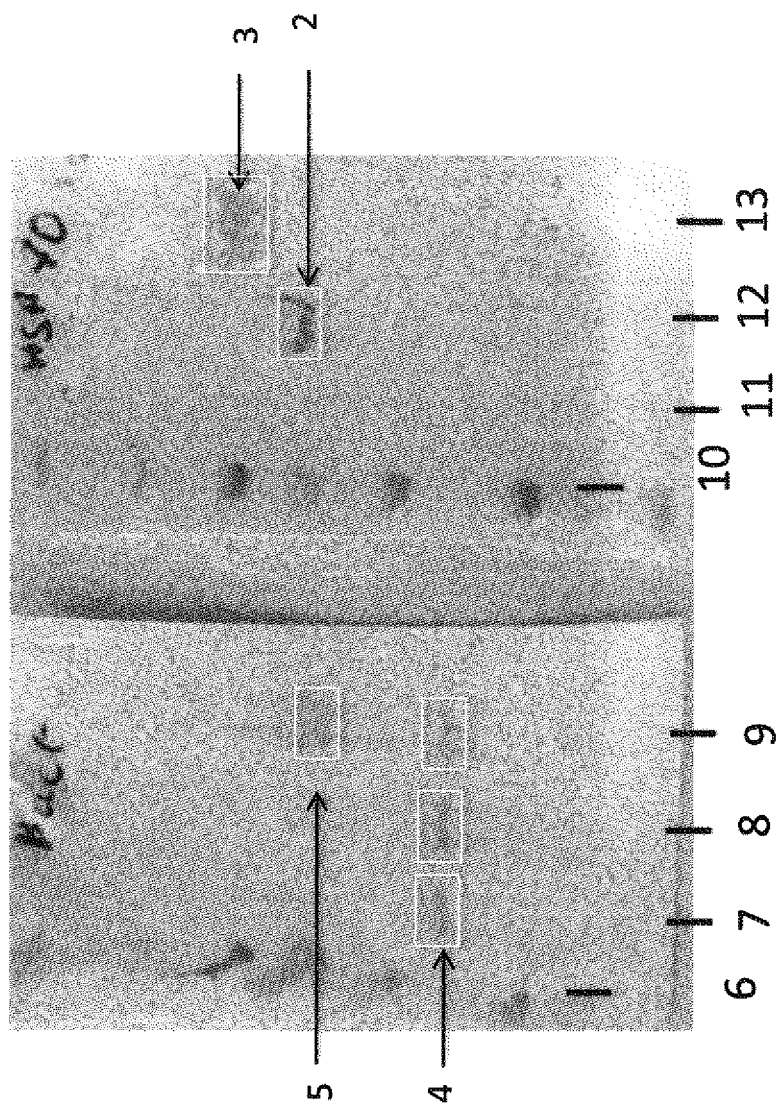
Figure 2:
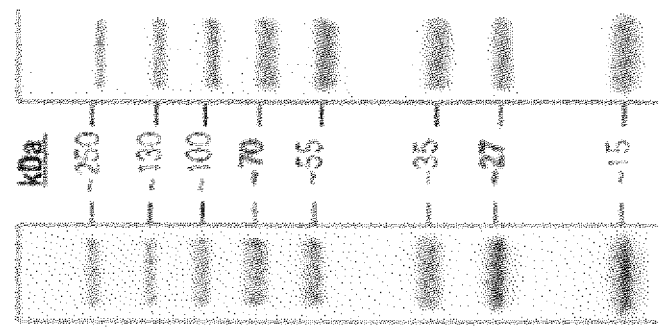

FIG. 2 is a Western Blot showing the induction of HSP 70 by heat stress and the haptenisation of HSP 70, with in parallel a Western Blot performed on a β-actin control. In order to ensure ease of reading, the main spots have been encircled. Identifying reference numerals: HSP 70 (2); HSP 70 haptenised (3); β-actin (4); β-actin haptenised (5); Molecular Weight Marker (6); CT26WT Cells treated for 1 hour at 37° C. (7); CT26WT Cells treated for 1 hour at 42° C. (8;) vaccine dose stressed, haptenised and irradiated (9); Molecular Weight Marker (10); CT26WT cells treated for 1 hour at 37° C.+14 hours at 37° C. (11); CT26WT cells treated for 1 hour at 42° C.+14 hours at 37° C. (12); vaccine dose stressed, haptenised and irradiated (13).

Figure 4:
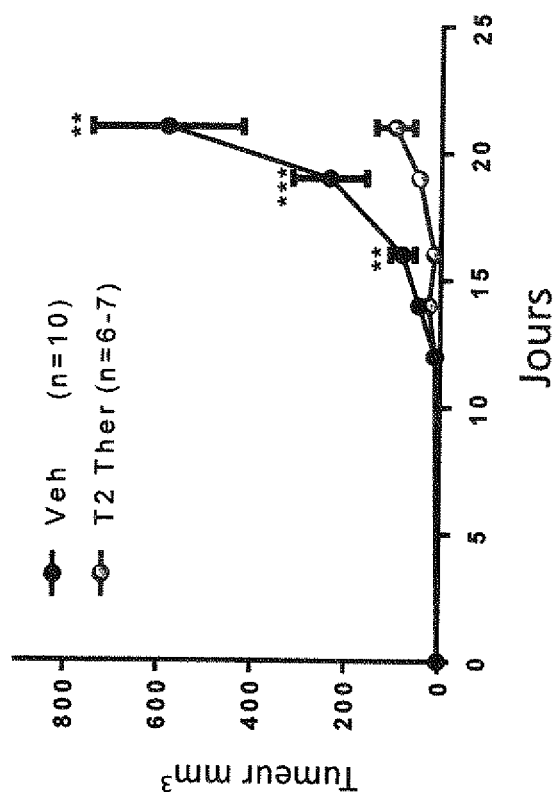
Figure 3:
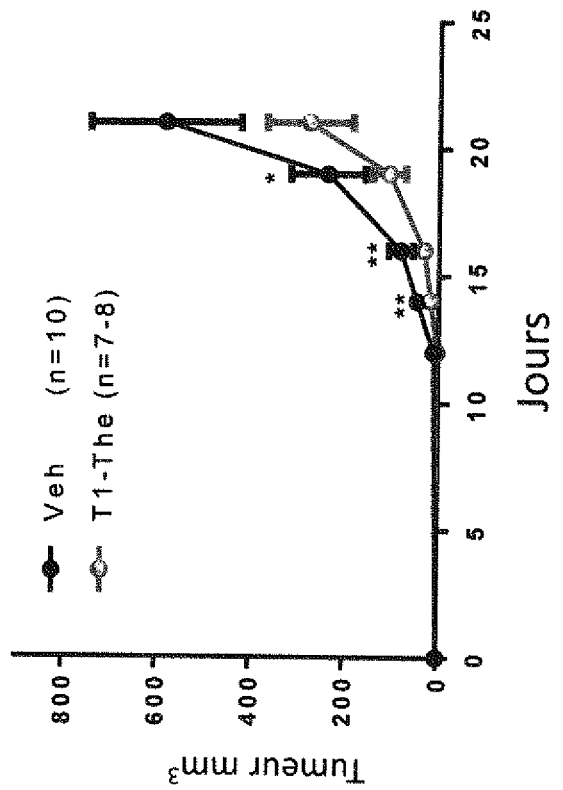

The FIGS. 3 and 4 are graphs each representing the evolving change over time of the volume of tumours induced in mice between the control mice injected with an excipient ("Veh" for "vehicle") and the mice treated with vaccines according to the invention ("The" for "Therapeutic").

Figure 5:
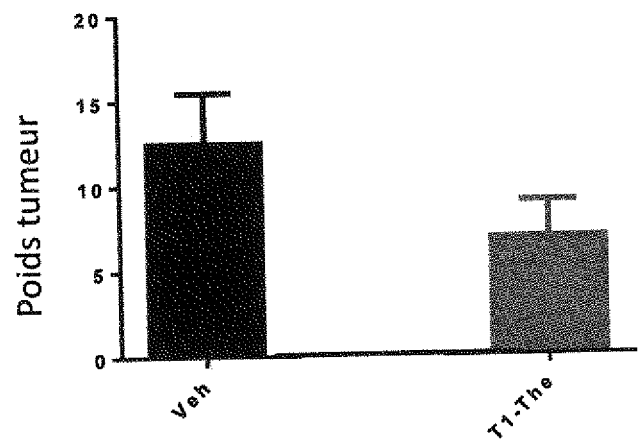
Figure 6:
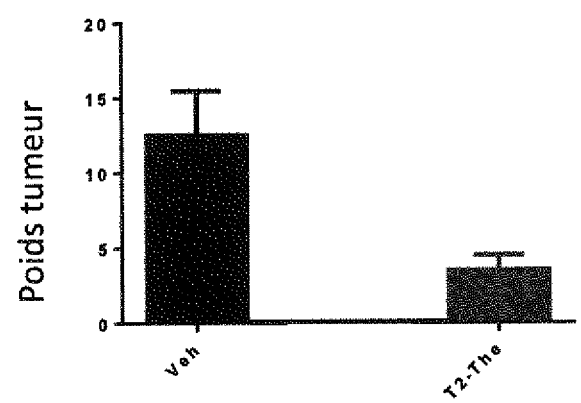

FIGS. 5 and 6 are graphs showing, for the same groups represented in the FIGS. 1 and 2, the weight of the tumour in grams induced in the mice at the time of resection ("Veh" for "vehicle" or excipient; "The" for Therapeutic).

EXAMPLE 1: METHOD FOR PRODUCING ALLOGENEIC DOSES

Cell Lines

The cell lines are derived from commercially available pre-established lines (ATCC type) or resulting from the constitution of the line derived from the patient sample, characterized, and tested. By way of example, the lines that are used include Caov, OVCAR-3, ES-2, and OV-3, for an ovarian cancer therapeutic target. They are cultured separately in the recommended conditions.

Patient Cells

The patient cells are isolated from the patient and cultured in a medium and under the appropriate conditions.

The cells from the cell lines and patient are subjected during the course of their growth phase or their plateau phase to a stress so as to enable the overexpression of factors of resistance (stress proteins).

Type of Stress Applied:

Irradiation 2 gray

Heat Shock: temperature rise up to 40° C.-43° C. with a plateau of 30 to 60 minutes Chemical shock with ethanol, cyclophosphamide, doxorubicin or cisplatin.

The expression of one or more factor(s) of resistance is confirmed by means of flow cytometry, Elisa or Western Blot). In particular by cytometry using the anti-HSP antibodies (anti-human HSP 27-FITC; anti-human HSP60-PE, anti-human HSP 72-FITC; anti-human HSP 90-PE).

The factors of resistance (stress proteins) expressed by the allogeneic cells are chemically labeled or tagged with Dinitrophelyl. By way of a variant use can be made of sulphanilic acid, N-iodoacetyl-N'-(5-sulfonic-naphthyl) ethylene diamine (EDA), aniline, or p-amino benzoic acid).

The allogeneic cells comprising the haptenised stress proteins are then rendered non-proliferative by high dose irradiation (25 gray). By way of a variant use may be made of ethanol fixation between 10% and 50% v/v or any other method that provides for the inhibition of cell proliferation while maintaining the cell structure intact.

The haptenised cellular stress proteins of allogeneic origin are distributed in the form of cell suspension in a formulation medium that is suitable for therapeutic use and allows for the preservation thereof at low temperature (−20° C., −80° C.), and then distributed in doses comprising from 1 to 5 $10^6$ inactivated and haptenised cells per dose corresponding to a therapeutic dose expressed in protein amount "HSP positive" and/or in organic matter amount. An immunizing adjuvant may be present, for example BCG, GM-CSF, IL2.

EXAMPLE 2: METHOD FOR PRODUCING AUTOLOGOUS DOSES

The cells are derived from the tumour of the patient after resection. The biological material is transported in a specific kit that makes possible its preservation while ensuring optimal viability of the cells.

The cells of the biopsy are dissociated by a suitable mechanical method, and then placed in suspension in a nutrient medium that provides for their growth or viability only.

The tumour cells are used as they are or following a selection by means of cell sorting.

The tumour cells in the expansion phase or in the stationary phase are subjected to a stress as defined in the production of allogeneic cells.

The expression of one or more factor(s) of resistance is confirmed according to an appropriate method of analysis, as in example 1.

The factors of resistance (stress proteins) expressed by autologous cells are chemically tagged by a method similar to that described for the allogeneic cells in Example 1.

The autologous cells including the haptenised stress proteins are rendered non-proliferative by the same method as that used for the allogeneic cells in Example 1.

The haptenised stress proteins integrated in the autologous cells, are distributed in the form of a cell suspension in a formulation medium that is suitable for therapeutic use and provides for their preservation and then distributed in therapeutic doses.

EXAMPLE 3: METHOD OF TREATMENT

The therapeutic treatment regimen includes the administration of:
  one or more allogeneic or autologous doses; or
  one or more allogeneic and autologous doses, administered together or in a sequential manner.

The administration of the product is by way of an intradermal injection. It is also possible to use another route of administration and in particular per os.

The product is administered alone or in synergy with any other therapy that allows for a potentiation of the treatment.

EXAMPLE 4: PRODUCTION OF HSPS

The CT26-WT line is a mouse colon carcinoma line, available under ATCC® CRL-263 8™. The cells grow easily and rapidly (doubling time 22 hours).

The HL60 line is a human cell line (Caucasian promyelocytic leukemia) available from Sigma-Aldrich®. The cells are frozen after the expansion.

The original cells had been received in frozen form. The cells were thawed, after which they were put to culture in flasks, in an appropriate culture medium. The culture medium was changed on D+1. After expansion, a count of the live cells was performed, then the concentration was adjusted to about $2·10^6$ living cells/ml of culture medium. A pool of $200·10^6$ cells was recovered, and then washed after confirming that the cells were at approximately 50% confluence. The suspension was then divided into 50 ml tubes based on 25 ml per tube. The tubes were then immersed in a water bath heated to 42° C. The tubes were allowed to remain for about 1 hour in the water bath. The cells were then transferred into the flasks at a rate of $2·10^6$ cells. Thereafter the cells were incubated for 14 hours at 37° C. The cell concentration was then adjusted to $5·10^6$ living cells/ml.

The cells were then haptenised with a solution of 2,4-dinitrofluorobenzene (DNFB) 0.07%. The haptenisation is revealed by labeling with FACS. FACS flow cytometry was chosen as the analytical technique, it provides the ability to give a percentage of cells haptenised in relation to the total number of cells.

The cell suspension is adjusted to a concentration of 2 to 5·10⁶ cells/ml with freezing medium and stored in a freezer at −80° C.±3° C. for a minimum of 24 hours before testing them.

The frozen cells were then subjected to irradiation by X-rays at 25 grays, in order to inactivate the tumour cells.

Two standard techniques were used to detect the expression of HSPs or haptenised HSPs; these same techniques can be used to detect any stress protein, by means of the antibody specific to the protein to be detected:

Western blot using the antibodies specific to the HSP to be detected.

Flow Cytometry (FACS, fluorescence-activated cell sorting) after tagging of the intracellular HSPs by using specific antibodies.

By way of specific antibodies, use was made of the commercially available anti-HSP 27 antibodies, anti-HSP 70 antibodies, anti-HSP 90α/β antibodies. According to the technique that was used, further use was made, as this is known per se, of additional antibodies, mouse IgG1, FITC conjugated sheep anti-mouse IgG, control antibody (anti-KLH-FITC), antibody (anti-TNP FITC), DNFB specific. Commercially marketed antibodies that are usable are available from Santa Cruz Biotechnology Inc. and BD Biosciences.

For the cytometry, the haptenised cells were thawed, they were subsequently washed and the concentration was adjusted from 1 to 2·10⁶ cells/ml. The following were deposited in a V bottom 96-well plate:

5 μl of control antibody (anti-KLH FITC) in two wells,
5 μl of antibody (anti-TNP FITC) in two wells.

Subsequently 100 μl of haptenised cell suspension was then added per well, and the plate was incubated for 15 minutes at +5° C.±3° C. Thereafter the cells were then washed, and the cell suspensions were transferred to tubes for passing over a "FACS Calibur". The "DNP-FITC" tubes were passed through according to the parameters fixed in advance with the control.

Results:
3. CT26-WT Line: Compared to the same line maintained at 37° C. for 1 hour, in Western blot a band is seen to appear at about 70 kD (FIG. 1) corresponding to HSP 70 in the stressed cells at 42° C. according to the protocol here above.

4. HL60 Line:

The analysis of control cells (1 hour at 37° C.+14 hours recovery time at 37° C.) and stressed cells (1 hr at 42° C.+14 hr recovery time at 37° C.) was performed by means of flow cytometry after intracellular labeling of HSP 27, 70 and 90 by the specific antibodies mentioned here above.

Results:

|  | % cells analysed (window) | Intensity Average of labelled cells |
|---|---|---|
| No stress | | |
| Positive Control | 92.07 | 59.42 |
| HSP 27 | 92.37 | 37.09 |
| HSP 70 | 92.14 | 7.85 |
| HSP 90 | 91.78 | 31.19 |
| Stress | | |
| Positive Control | 71.56 | 68.11 |
| HSP 27 | 72.07 | 71.90 |
| HSP 70 | 70.47 | 30.90 |
| HSP90 | 70.32 | 57.03 |

An overexpression of HSPs and more specifically of the HSP 27 and 70 in the stressed cells is noted.

EXAMPLE 4: ANIMAL TESTING

The production of tumour doses consisted in bringing about expansion of the CT26.WT cells, followed thereafter by a freezing in the culture medium supplemented with 5% DMSO and at a rate of 6.25·10⁴ cells in 25 μl final.

The production of vaccine doses consisted in bringing about the expansion of the CT26.WT cells, then after 2 passages the cells were subjected to a heat stress for 1 hr at +42° C. followed by a recovery time of 14h at 37° C. Then, the cells were haptenised (by DNFB, dinitrofluorobenzene), then frozen at −80° C. based on 6.25·10⁵ cells in 250 μl final and finally the vaccine doses were irradiated (25 Gray).

Controls were performed for the tumour and vaccine doses:

Tumour doses production of the tumour in animals):
Sterility by blood cultures→negative blood cultures
Control of endotoxins.→endotoxins ≤200 IU/ml
Control of cell number and viability of tumour doses.→amount comprised between 5.5 and 6.95·10⁵ cells, viability ≥95%.

Vaccine doses:
Sterility by blood cultures:→negative blood cultures.
Control of endotoxins: 2→endotoxins ≤200 IU/ml
Control of the haptenisation by FACS labeling with the use of the anti-KLH-TNP antibody: →haptenisation %≥96%
Control of the cellular quantity of tumour doses: →amount between 5.96 and 6.10·10⁵ cells),
Control of the expression of HSP by cytometry using the specific antibodies mentioned here above: →the expression of HSP 27, 70 and 90 was detected.
Control of detection of HSP by Western blot using the specific antibodies mentioned here above: →the FIG. 2 shows a HSP 70 spot after thermal stress and a haptenised HSP 70 spot.
Viability test in order to ensure that the cells of the vaccine composition are not proliferative: addition of propidium iodide+putting to culture; the lack of proliferative capacity of the cells that make up the vaccine doses was confirmed

EXAMPLE 5: IN VIVO STUDY IN MICE

BALB/c male and female mice aged 6 to 8 weeks, obtained from Charles River, were used. 5 mice were placed per 16×19×35 cm cage under controlled temperature (22±2° C., in alternating lighting conditions (12 h cycles of day and 12 hours of dark) and supplied with water and food ad libitum. The mice were acclimated for at least 1 week before starting the experiments.

The tumour model is the subcutaneous CT26 carcinoma (CT26WT, ATCC ° CRL-2638™), which is a syngeneic tumour model commonly used for the study of therapeutic applications against cancer in animals, in particular for testing immunotherapy protocols and study the immune response.

50 female mice were divided into 5 groups of 10. Each mouse was injected subcutaneously (SC) on day 0 (D0) with 5·10⁴ CT26WT tumour cells. The treatment protocol was as follows:

Group 1: excipient
Group 2: therapeutic treatment 1
Group 3: therapeutic treatment 2

Cyclophosphamide was administered by injection at 15 mg/kg via the intraperitoneal route (IP) on D+2 to the groups 2 and 3.

Treatment 1 (BCG IL-2/vaccine) for the group 2:
BCG: $2·10^6$ CFU (colony forming units) per SC injection
Recombinant murine IL-2: 4 000 IU per SC injection
Vaccine: $5·10^5$ CT26WT cells (irradiated and haptenised) by SC injection.

Treatment 2 (BCG/GM-CSF/vaccine) for the group 3:
BCG: $2·10^6$ UFC by SC injection
Recombinant murine GM-CSF: 25 000 IU (international unit) via SC route
Vaccine: $5·10^5$ CT26WT cells (irradiated and haptenised) by SC injection Protocols:

| Day | Treatment/route | Group 1 | Group 2 | Group 3 |
| --- | --- | --- | --- | --- |
| D 0 | SC CT26WT | X | X | X |
| D + 2 | IP | | X | X |
| D + 7 | Cyclophosphamide | Excipient | T1 | T2 |
| D + 14 | SC Treatment | Excipient | T1 | T2 |
| D + 21 | SC Treatment | Excipient | T1 | T2 |
| D + 28 | SC Treatment SC Treatment | Excipient | T1 | T2 |

Parameters measured during the course of the study, and other specifications:

Daily monitoring of the behaviour of the mice.

Monitoring 3 times per week of the body weight and tumour volume. The tumour volume in $mm^3$ was calculated using the formula: volume=$[(width)^2 \times length]/2$. Measure dimensions with the help of a caliper.

The mice are sacrificed in case of signs of unexpected distress.

The mice were sacrificed when the tumour reached 1000 $m^3$ and in any case no later than 40 days after implantation of the tumour. The tumours were excised and measured.

The results of measurement of the tumour volume in $mm^3$ over time show a favorable impact of both the two therapeutic vaccines T1 and T2 as compared to the control mice: See FIGS. 3 and 4.

The results of measuring of the weight of the tumours after resection also showed a favorable impact of the vaccines T1 and T2 as compared to the control mice: see FIGS. 5 and 6.

What is claimed is:

1. A pharmaceutical composition or vaccine comprising tumor cells, a plurality of different immunogenic stress proteins, and a pharmaceutically acceptable excipient, wherein said tumor cells developed a viable resistance mechanism in response to a stress applied in vitro thereto, said plurality of different immunogenic stress proteins also produced by said stress applied in vitro to said tumor cells, and wherein said stress applied in vitro to said tumor cells is selected from the group consisting of irradiation, heat shock, chemical shock, metabolic stress, and combinations thereof.

2. The pharmaceutical composition or vaccine according to claim 1, wherein the tumor cells are bearing or containing haptenized stress proteins.

3. The pharmaceutical composition or vaccine according to claim 1, wherein the tumor cells are selected from the group consisting of cell line cells, a combination of cells from allogeneic cell lines, cells from the patient, and a combination of cells from allogeneic cell lines and patient's cells, said tumor cells bearing or containing haptenized stress proteins.

4. The pharmaceutical composition or vaccine according to claim 1, wherein the stress proteins in said plurality of different immunogenic stress proteins are selected from the group consisting of heat shock proteins, radioresistant proteins, chemotherapy resistant proteins, metabolic stress resistant proteins.

5. The pharmaceutical composition or vaccine according to claim 1, further comprising an adjuvant.

6. The pharmaceutical composition or vaccine according to claim 1, wherein the stress proteins are haptenized.

7. The pharmaceutical composition or vaccine according to claim 1, wherein said stress proteins are distributed in the composition inside the tumor cells, bound to a tumor cell surface or fragment thereof, and/or outside the tumor cells.

8. The pharmaceutical composition or vaccine according to claim 1, wherein tumor cells are cells from one or more tumor cell lines.

9. The pharmaceutical composition or vaccine according to claim 1, wherein the stress proteins are selected from the group consisting of stress proteins caused by a chemotherapeutic drug, stress proteins caused by irradiation, stress proteins caused by heat, stress proteins caused by metabolic stress, and stress proteins caused by irradiation and heat.

10. The pharmaceutical composition or vaccine according to claim 1, wherein the composition is formed from at least two allogeneic line tumor cells that have been subject in vitro to a stress selected from the group consisting of irradiation, heat, chemical, metabolic stress, and combinations thereof, during the culturing thereof, and each one of the at least two allogeneic line tumor cells has undergone treatment capable of rendering its stress proteins immunogenic.

11. The pharmaceutical composition or vaccine of claim 10, wherein the at least two stressed allogeneic line cells are formulated as a kit of parts.

12. The pharmaceutical composition or vaccine according to claim 1, wherein said tumor cells were rendered non-proliferative after having produced the plurality of stress proteins.

* * * * *